United States Patent [19]

Kreikebaum

[11] 4,140,395

[45] Feb. 20, 1979

[54] ELECTRO-OPTICAL METHOD AND SYSTEM FOR IN SITU MEASUREMENTS OF PARTICLE SIZE AND DISTRIBUTION

[75] Inventor: Gerhard Kreikebaum, Knoxville, Tenn.

[73] Assignee: Environmental Systems Corporation, Knoxville, Tenn.

[21] Appl. No.: 748,199

[22] Filed: Dec. 7, 1976

[51] Int. Cl.² ............................................ G01N 15/02
[52] U.S. Cl. ..................................... 356/336; 250/574
[58] Field of Search ....................... 356/102, 103, 104; 250/574

[56] References Cited

U.S. PATENT DOCUMENTS

| | | | |
|---|---|---|---|
| 3,797,937 | 3/1974 | Shofner | 356/102 |
| 3,914,058 | 10/1975 | Knapp | 356/103 |
| 4,017,186 | 4/1977 | Shofner et al. | 356/103 |

OTHER PUBLICATIONS

Knollenberg et al., "Open Cavity Laser 'Active' Scattering Particle Spectrometry From 0.05 to 5 Microns", 670–681.

*Primary Examiner*—Conrad J. Clark
*Attorney, Agent, or Firm*—Fitch, Even, Tabin & Luedeka

[57] ABSTRACT

A system and method provides in situ measurements of the size of particulate matters suspended in fluid medium. A beam of intermittently interrupted electromagnetic radiation is directed through a portion of the fluid medium and radiation backscattered from a first optically defined region disposed within the fluid medium at a location having substantially uniform incident illumination is detected and utilized to provide an indication of the size and distribution of the suspended particles. To assist in assuring particles under surveillance are within the first region at the time the measurements are made, light backscattered from a further region disposed in the fluid medium and containing the first region is collected and compared with the intensity of the radiation backscattered from the first region prior to making the measurements.

13 Claims, 4 Drawing Figures

ELECTRO-OPTICAL METHOD AND SYSTEM FOR IN SITU MEASUREMENTS OF PARTICLE SIZE AND DISTRIBUTION

The invention relates to the in situ electro-optical measurement of particles suspended in a fluid medium. More particularly the invention relates to a method and apparatus in which electromagnetic radiation such as light is directed into a fluid medium containing suspended particles and the intensity of backscattered light is utilized to indicate the size and distribution of the suspended particles.

In in situ particle measurements, a beam of electromagnetic radiation such as light is directed into the particle carrying fluid medium and the size of the particle is inferred by interpreting the backscattered light. Accuracy in interpreting the size of the particles is dependent in part upon the intensity of the illumination incident on the particles being constant. In devices in which flow of the particles contained in the fluid medium is controlled, uniform illumination of particles can be assured as by passing a fluid medium laden with particles through a tube for example, into a preferred scattering volume or region of substantially uniform illumination. In the in situ device, however, no control is exerted over the flow of particles, and particles randomly occupy the volume defined by illuminated portions of the fluid medium of interest. If the illumination is not constant across the portion of the fluid medium containing particles under surveillance, different amounts of light will be scattered from identically sized particles and specious data may result. For example, where the source of illumination is a beam of light such as that produced by a laser, the intensity of the illumination decreases at locations radially spaced from the axis of the beam. For this reason, a 10 micron particle, for example, will scatter a different amount of light if positioned at radially spaced locations within the beam. A straight analysis of the amount of light scattered would result in an interpretation that identically sized particles were of different sizes if disposed at locations where the incident illumination is of different intensities.

Certain attempts have been made in the past to provide systems and methods for taking in situ measurements of the size and distribution of particles suspended in a fluid medium. One such system is described in a publication entitled, "Open Cavity Laser 'Active' Scattering Particle Spectrometry From 0.05 to 5 Microns", coauthored by Robert G. Knollenberg and Robert Luehr of Particle Measuring Systems, Inc., of Boulder, Colorado. This system utilizes a continuous laser for tracking particles through a pedetermined two-dimensional region and the size and distribution measurements are made during residence of the particles of interest within that section of the predetermined region having substantially constant illumination. Utilization of a continuous illumination source suffers certain disadvantages, however, and in certain applications it is preferable to use an intermittently interrupted illumination source. For example, the data rate with a continuous illumination source is random in that particles randomly enter and exit the sampled region which makes processing the data more difficult than with a light source which is interrupted at a known rate and produces data at a known rate. Moreover, the power consumption is less with an intermittently interrupted source for a preselected illumination intensity which enables packaging the interrupted source system in a smaller volume for a given intensity requirement.

It is therefore an object of this invention to provide an improved in situ particle size and distribution measurement system. It is another object of the invention to provide an improved method for making in situ particle size and distribution measurements. It is a further object of this invention to provide such a system and method utilizing an intermittently interrupted illumination source which illuminates a portion of the fluid medium in which the particles of interest are suspended. Another object of the invention is to provide an optically defined sampling volume in which the illumination is constant. A further object of the invention is to provide means to assure that the particles under surveillance are within a predetermined region or sampling volume having substantially uniform intensity at the time measurements regarding the size and distribution of the particles are made.

Other objects and advantages will become apparent upon reading the detailed specification together with the drawings wherein.

The present disclosure is directed to an electro-optical system and method for in situ determinations of the sizes and distribution of particulate matter suspended in a fluid medium. A beam of intermittently interrupted electromagnetic radiation is directed through a portion of the medium and radiation backscattered from first and further optically defined regions, the first region being contained in the further region, is detected and utilized to provide an indication of the size and distribution of particles suspended in the fluid medium. To assist in assuring residence of particles under surveillance within the first volume which is transilluminated by substantially uniform intensity, the radiation backscattered from the first and further regions or volumes respectively are compared prior to making measurements concerning the size and distribution of particles.

Figures 1, 2:
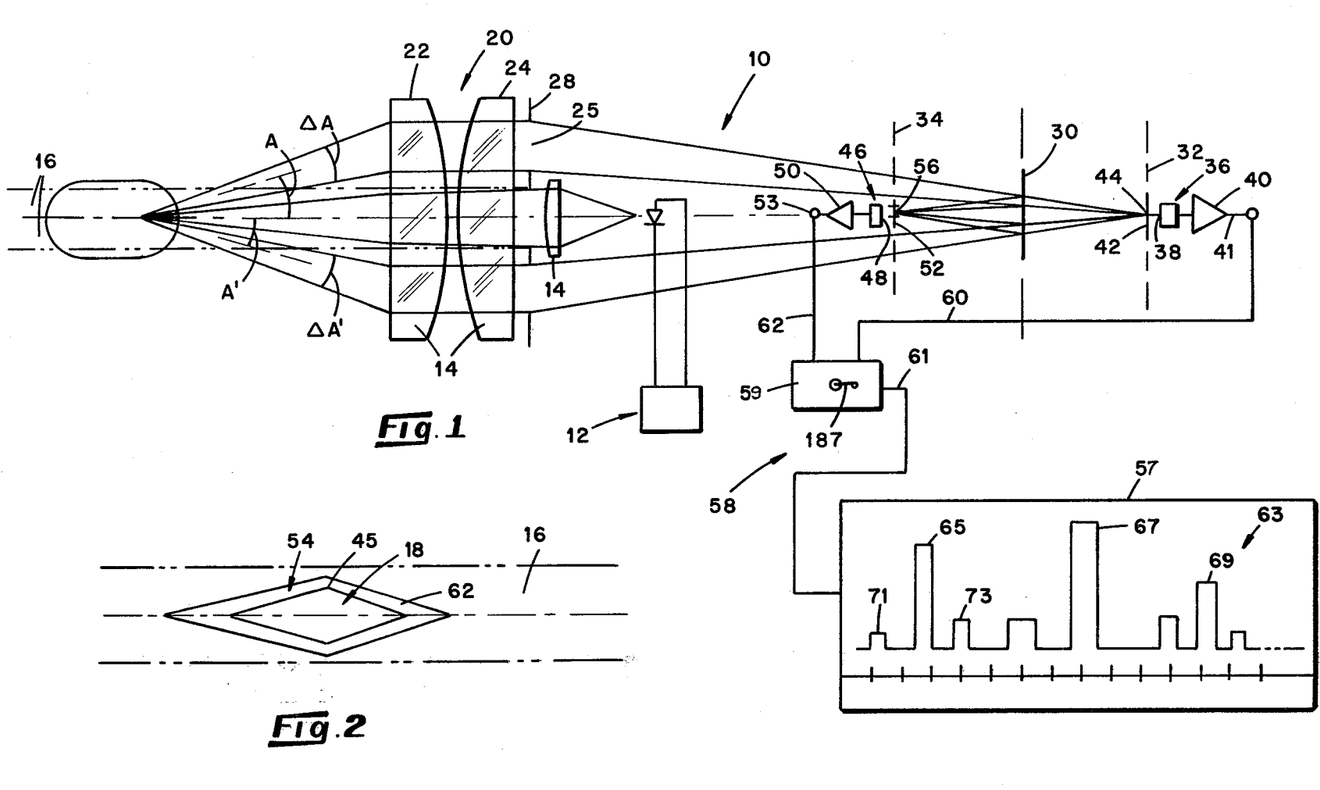
FIG. 1 is a schematic representation of a particle measurement system embodying various features of the invention.
FIG. 2 is a schematic representation of a cross section of the sampling volumes, the smaller sampling volume being the location of the particles under surveillance.

Referring now to the Figures, the system illustrated schematically at 10 in FIG. 1 finds particular application in measuring in situ the size and distribution of particles suspended in a fluid medium, such as process gases. The system 10 is adapted for being positioned proximate a fluid medium containing particles of interest and in this connection may be mounted in a portable housing.

The system 10 includes a source of substantially monochromatic electromagnetic radiation indicated generally at 12 which serves to generate a beam of light for illuminating a portion of the fluid medium containing the suspended particles. The source 12 is intermittently interrupted for illuminating particles passing through the beam at predetermined intervals. Utilization of an intermittently interrupted or pulsating source 12 serves to reduce the power consumption and operational cost of the system. One particularly suitable radiation source is a pulsating laser of the junction diode type adapted for emitting infrared radiation such as a GaAs PN-junction laser which emits 200 nanosecond pulses. Preferably, the rate of pulsing is chosen in conjunction with the velocity of particle and the cross sectional dimension of the region in which the particles under surveillance reside when the measurements are made to the end that there is a single exposure of a given particle during the period of its transience across the scattering volumes. Accordingly, no particle is exposed to the intermittently interrupted light beam more than once during its passage through this region or sampling volume in one embodiment of the invention. Consequently, only one measurement is taken for each particle under survelliance.

It will be recognized, however, that the pulsing rate of the source 12 may be chosen such that a single particle is illuminated a plurality of times during its residence within the sampling volume and the size and distribution of the particles determined by a different interpretation of the resulting data. For example, if a single particle is illuminated a plurality of times such as by multiple firing of the laser during the particles transience across the sampling volume, a gaussian shaped intensity curve would result. In this connection the system is inherently isokinetic in that there is no dependence on the flow velocity of the fluid medium carrying the particles of interest.

Light generated by the source 12 is directed through a portion of the fluid medium containing the particulate material for transillumination of the sampling volume. In this connection, light emerging from the source 12 in FIG. 1 passes through beam forming optics including substantially parallel disposed collimating lenses generally indicated at 14 which serve to form a substantially collimated beam 16 which exits the system 10 through a suitable aperture (not shown in FIG. 1) and is directed through a portion of the medium through which the particulate matter under surveillance passes. As necessary or desired, the collimating lenses may be adjusted to vary the width of the beam 16.

The beam 16 produced by the source 12, such as a laser, is preferably circular in cross section and the intensity variations of the beam are kept within acceptable limits. As is common knowledge, however, the intensity across the cross section of the beam varies radially with respect to the axis of the beam, i.e., the intensity near the outer margin of the beam is less than the intensity near the axis of the beam. In order to assist in assuring substantially identical illumination of the particles under surveillance, radiation is accepted for measurement purposes only if the particles reside in a predetermined sampling volume 18 which is optically defined and substantially uniformly illuminated.

More specifically, only particles residing in the optically defined three dimensional region or sampling volume 18 backscatter light which is accepted for determining the size and distribution of the particles within the fluid medium. To this end, the sampling volume 18 is defined by first optical means which serve to collect light backscattered along predetermined paths from the sampling volume 18 and direct such light toward a photodetector to be described in greater detail hereinafter. As shown in the schematic diagram of FIG. 1, the illustrated optical means include lenses 22 and 24 which serve both to collimate the beam 16 and to focus light passing through their respective annular margins onto an image plane generally indicated at 32 for reasons which will be pointed out in more detail hereinafter. A portion of the light backscattered by particles in the fluid medium passes through the annular margins of lenses 22 and 24 and through the annular aperture 25 defined by the aperture means 28. In the illustrated embodiment the aperture 25 serves to collect electromagnetic radiation backscattered substantially along angles A and A' and within the ranges of $\Delta A$ and $\Delta A'$ and is coaxially aligned with the beam 16 for collecting backscattered radiation symmetrically around the beam. In the embodiment illustrated in FIG. 1 angle A is equal to angle A', and $\Delta A$ is equal to $\Delta A'$. It has been found that by collecting the radiation backscattered by about 170° as measured clockwise and counterclockwise, respectively, from the axis of the beam exiting the sample volume, and within a range of approximately 5°, accurate measurements can be made concerning the size and distribution of particles suspended in the fluid medium.

It will be recognized that the angle between the incident illumination, i.e., the laser beam 16, and the collected radiation which is scattered from the particles may vary from approximately 0° to approximately 180°. For example, the collecting optics could be positioned on the opposite side of the sampling volume 18 from the source 12 as necessary or desired. The particular arrangement shown in FIG. 1, however, utilize lenses 22 and 24 both in forming the beam 16 and in collecting the scattered radiation.

To assist in assuring that particles under surveillance are illuminated by a substantially identical amount of incident illumination, i.e., to assure location of particles within the first region or sampling volume 18 at the time measurements concerning the size and distribution of the particles are made, light backscattered from particles within the sampling volume 18 and collected by the optical means is separated into predetermined amounts of electromagnetic radiation by a beamsplitter 30. More specifically, the illustrated beamsplitter 30 is substantially coaxially aligned with the beam 16 and is interposed in the path of the backscattered radiation focused on the image plane 32 of the sampling volume 18 by lens pair 20. The illustrated beamsplitter 30 is disposed substantially parallel with respect to lenses 22 and 24 and fabricated from a partially reflective and partially transmittal material which serves to pass and to reflect predetermined portions of the incident backscattered radiation. The angle of incidence of the backscattered radiation on the beamsplitter 30 is substantially identical to the angle of emergence of the portion of radiation transversing the beamsplitter toward the image plane 32. Moreover, the angle of incidence of the reflected portion of the radiation is substantially identical to the angle of reflection of this radiation.

It will be recognized that the image planes of the sampling volume 18 as defined by the portions of the backscattered radiation transversing and reflected from the beamsplitter 30 lie along the imaginary planes 32 and 34, respectively, which are aligned substantially parallel with respect to beamsplitter 30 and disposed equal distances from the beamsplitter.

A portion of the light passing through beamsplitter 30 is incident on photodetector means 36 disposed behind the beamsplitter 30 with respect to the sampling volume 18. The photodetector means 36 is of known design, one suitable photodetector means including a silicone photodiode-preamplifier combination, for example, the MDA321 photodector manufactured by Meret, Inc. This photodetector means 36 includes a first photosensitive medium 38 which serves to produce electronic signals systemmatically related to the intensity of the electromagnetic radiation backscattered from the sampling volume 18 and falling on the photosensitive medium. The electronic signals generated by the photosensitive medium are fed to a conventional amplifier 40 which serves to amplify the electronic signals and produce such amplified signals at its output 41.

The portion of the light accepted by the photosensitive means is determined by aperture means 42 interposed in the path of the backscattered radiation directed from the beamsplitter 30 to the photodetector means 36. This aperture means 42 serves to determine the amount of light accepted from the sampling volume 18 and is disposed within the image plane of such sampling volume as determined by lenses 22 and 24. More specifically, the sampling volume 18 comprises the projected image of the aperture 44 with the widest portion 45 (See FIG. 2) of the sampling volume 18 being identical to the width of the aperture 44 if the magnification of the lenses 22 and 24 is equal to one.

Similarly, a portion of the backscattered radiation reflected by beamsplitter 30 is incident upon further photodetector means 46 of conventional design which is disposed in the illustrated embodiment on the opposite side of beamsplitter 30 from photodetector 36. The photodetector 46 includes a photosensitive medium 48 which serves to produce electronic signals systemmatically related to the intensity of the incident electromagnetic radiation. The electronic signals generated by the photodetector means 46 are fed to a conventional amplifier 50 which serves to amplify the electronic signals and produce such amplified signals at its output 53.

The portion of the electromagnetic radiation incident on the photodetector means 46 is determined by the aperture means 52 interposed between the photodetector 46 and the beamsplitter 30 along the path of light reflected from the beamsplitter 30 toward the photodetector 46. Aperture 56 defined by aperture means 52 serves to determine the shape and size of the sampling volume 54 within the fluid medium from which backscattered radiation is accepted by the photodetector 46 and is disposed within the image plane of such sampling volume 54.

As illustrated in FIG. 1, the image planes of sampling volumes 18 and 54 are spaced equal distances of the beamsplitter 30. Preferably, the apertures 44 and 56 are circular in outline and define the conical shaped sampling volumes, as shown in FIG. 2 which have diamond shaped cross sections. As necessary or desired, however, different shaped apertures and sampling volumes may be used.

The outputs of the photodectors 36 and 46 are fed through leads 60 and 62 to indicator means 58 adapted to convert the signals to a usable form for indicating the size and distribution of particles suspended in the fluid medium. The illustrated indicator means may comprise any one of several possible devices, for example, the output signals may be fed to a conventional oscilloscope, a tape recorder, a digital counter, a pulse height analyzer or a mini-computer with or without a readout. In the illustrated embodiment the indicator means 58 comprises a microprocessor based pulse height analyzer 59 of conventional design. The pulse height analyzer is programmed to produce an output at 61 which may be adapted to drive a printer, for example, for producing a usable form of information as will be pointed out in greater detail hereinafter.

The signals representative of the intensity of the radiation backscattered from the first and further regions 18 and 54 shown in FIG. 2 are compared to determine the location of the particles prior to making measurements indicative of the size and distribution of the particles suspended in the fluid medium. Assuming that the transfer functions including gain for the apparatuses associated with each channel are identical only when the magnitude of the signals generated by the first and further photodetector means 36 and 46, respectively, are equal will the measurement be made. (Compensations are made in the physical apparatus to accommodate variations in the transfer functions for the apparatus associated with each sampling volume, as will be pointed out in greater detail hereinafter.) Assuming identical transfer functions, it will be recognized that where the magnitude of the signals representative of the intensity of the radiation backscattered from the first and further regions 18 and 54, respectively, are equal, no particles lie within the region 62 which is within the further region 54 and outside the first region 18. Particles residing within the first region 18 are illuminated with electromagnetic radiation of substantially identical intensity and therefore there is a systemmatic correlation between the size of the particles and the backscattered radiation. Moreover, the volume of the fluid medium contained within the region 18 is predetermined inasmuch as it is the projected volume defined by the aperture 44 interposed between the beamsplitter 30 and the photodetector 36. In this connection the volumetric concentration of the particles is determined by comparing the volume of the fluid sampled with the number for particles detected. More specifically, the concentration of particles suspended in the fluid medium is determined by dividing the number of particles by the volume of the fluid sampled, which is equal to the volume of the region 18 multiplied by the number of times the laser 12 fires. Similarly, the mass concentration of the particles suspended in the fluid medium is determined by dividing the mass of the particles by the volume of the fluid sampled, i.e., the volume of region 18 multiplied by the number of times the laser 12 has fired. The mass of the particles can readily be determined by multiplying the density of the particles by the particle size, which is proportional to the intensity of the backscattered radiation. Such calculations are made by the indicator means 58, suitable indicator means as pointed out before comprising in one embodiment of the invention a microprocessor-based pulse height analyzer 59. This information may be printed on hard copy tape or the like generated by the printer 64 which is drivingly connected to the indicator means 58.

Figure 4:
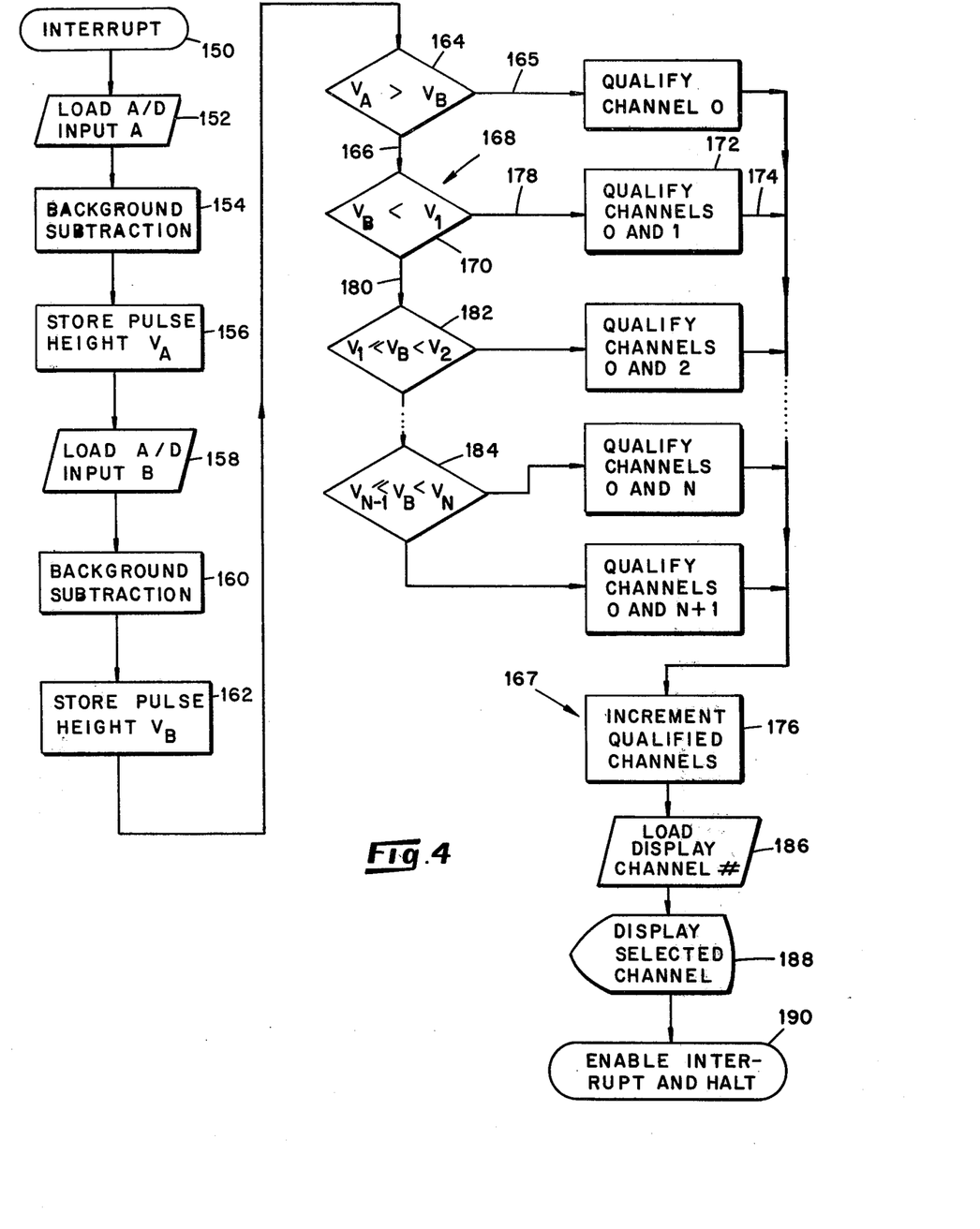
FIG. 4 is a flow diagram illustrating various of the operational steps of the system.

A flow diagram illustrating the operational steps of the microprocessor-based pulse height analyzer during assimulation and processing of the information signals produced at the outputs of amplifiers 40 and 50 is shown in FIG. 4. More specifically, the first block 150 serves as an interrupt to begin the operation sequence upon receipt of an input or command signal from leads 60 and 62 as when the laser 12 fires. The operational mode of the pulse height analyzer 59 is entered upon receipt of such a command signal and further command signals are blocked until the operational mode is completed.

Upon entering the operational mode, the analogue output or voltage pulse with a height $V'_A$ of the amplifier 40 which is representative of the intensity of the radiation backscattered from region 18 is converted into a digital signal by a conventional analogue to digital converter (not shown) housed in the pulse height analyzer 59 in the illustrated embodiment. The digital information is then fed into a microprocessor as indicated at the output of block 152. The microprocessor then performs background subtraction as indicated at 154 and discussed in greater detail hereinafter to produce a net pulse height $V_A$. The height or magnitude ($V_A$) of the digitized signal representative of the intensity of the radiation backscattered from the sampling volume or region 18 is then stored in the microprocessor memory as indicated at 156.

Similarly, the analogue output or voltage pulse with a height $V'_B$ of the amplifier 50 representative of the intensity of the radiation backscattered from the further region 54 is converted into a digital signal by a conventional analogue to digital converter (not shown) housed in the pulse height analyzer 59 as indicated at block 158 of the flow diagram shown in FIG. 5. This digital signal is then fed into the microprocessor (not shown) of the microprocessor-based pulse height analyzer as indicated at the output of block 158. The microprocessor then performs background subtraction as indicated at 160 and discussed in greater detail hereinafter and the net pulse height signal $V_B$ is produced. The magnitude or height of the digitized signal ($V_B$) representative of the intensity of the radiation backscattered from the sampling volume or region 54 is then stored in the memory as indicated at 162.

The two pulses are then compared by the microprocessor in order to determine the location of the particles which backscatter radiation from the scattering volumes to the end that measurements are made only if the particle or particles under surveillance are with region 18 which is substantially uniformly illuminated. In this connection, measurements are made only if the radiation backscattered from the first and further sampling volumes are substantially identical. The apertures which determine the sampling volume geometry and the amplifiers are adjusted to the end that when the net signal $V_A$ is greater than the net signal $V_B$, the yield from the respective sampling volume is substantially identical. More specifically, if $V_A$ is less than $V_B$, i.e., if the magnitude of the intensity of the radiation backscattered from the inner sampling volume 18 is not greater than the magnitude of the intensity of the radiation backscattered from the outer sampling volume 54, then the particles under surveillance are not confined within the inner sampling volume 18 having a substantially uniform illumination at the time the laser 12 is fired and no measurement of the particle size is made and a signal will be produced at branch 165 connected to block 164 which qualifies channel "0" only, channel "0" being the channel which increments upon each firing of the laser 12 regardless of the presence of a particle within the sampling volume 18. To this end, channel "0" is incremented by the operational steps generally indicated at 167 and described in greater detail hereinafter. In this event, only channel "0" will qualify and increment.

If a particle under surveillance resides within the inner sampling volume 18, the particle is classified according to size into one of a number of predetermined channels from 1 to N+1 with each of the channels being representative of particle sizes within a predetermined range. To this end, the string of decision blocks generally indicated at 168 serve to classify the particles residing within the substantially uniformly illuminated region 18 by sequentially determining if the voltage $V_B$ falls within a given range. If one of the inequalities indicated in the decisional string 168 is satisfied, the corresponding information is stored in an appropriate channel counter for display to indicate that a particle having a size within a predetermined range is detected. For example, if the particle size as represented by the digitized voltage signal $V_B$ is less than a predetermined value $V_1$, as illustrated by decisional block 170, then channels "0" and "1" are qualified as indicated at 172 by a command produced at branch 174 connected to block 172 which orders the microprocessor to increment the qualified channels as indicated at 176. More specifically, upon determining that $V_B$ is less than $V_1$, channel "0" is qualified (Block 172) and incremented (Block 176) to increase a conventional counter providing a cumulative count of the number of times the laser 12 has fired. Moreover, channel 1 is qualified and incremented by one to indicate that a particle is detected having a size smaller than the size represented by the voltage $V_1$.

Similarly, if the size of the particle within the region 54 is greater than or equal to the particle size represented by $V_1$, a "no" command is produced at branch 178 connected to block 170 and a "yes" command is produced at branch 180 connected to block 170, to the end that the particle size will be classified within predetermined ranges greater than particle size represented by $V_1$.

If branch 180 connected to block 170 indicates the particle to be classified according to size is equal to or larger than the size representated by $V_1$, and not less than the particle size represented by $V_2$ then channels 0 and 2 will be qualified and incremented. If the particle to be sized is larger than or equal to the size represented by $V_2$ then neither channels 0, 1 nor 2 will be qualified and the signal information ($V_B$) will pass through to the further decisional blocks 182 and 184, for example, for classifying the particle according to size upon satisfaction of the illustrated inequalities. If the particle to be sized is equal to or larger than the upper limit of the size range required for qualifying channel N, channel N+1 and channel 0 are qualified and incremented. Channel N+1 provides an overflow which is incremented upon the detection of a particle larger than the size represented by $V_N$.

Upon detection of a particle with the range of one of the channels 1 — N+1 illustrated in FIG. 4 that channel is qualified and a counter (not shown) operatively associated with the channel together with a counter operatively associated with channel "0" are incremented as illustrated at block 176.

In order to selectively display the number of particles detected with a given size range, a suitable multipositional switch 187 is provided on the pulse height analyzer 59 to select a predetermined channel for display. To this end, the microprocessor reads the position of the switch 187 (see block 186) and displays the selected channel indicated at block 188 on a suitable digital display (not shown).

After a particular particle has been sized or a determination is made that a particle is not within the region 54, the sizing and incrementing processes are halted and the interrupt is again enabled for processing further information taken at the output of amplifer 40 and 50 upon the laser 12 firing again.

Where a conventional pulse height analyzer 59 is used to drive a printer, the microprocessor may be programmed to sort the particle sizes into different ranges. One typical printout is shown below.

| EXAMPLE PRINTOUT | |
|---|---|
| 1. 1.0–2.0 (μm) | 012345 |
| 2. 2.0–3.0 (μm) | 008511 |
| . | |
| 7. 8.0–10.0 (μm) | 000358 |
| 8. (Laser Pulses) | 999999 |

The left-hand column following the numbers 1, 2 ... 7, indicates the diameter range of the particles and the corresponding right-hand column provides an indication of the number of particles within the corresponding range. The number of laser pulses is indicated as the last entry in right-hand column in the sample print-out. As indicated hereinbefore, the volumetric concentration of the particles can readily be determined by counting the number of particles and dividing the particle count by the volume of the fluid sampled which is equivalent to the volume of region 18 multiplied by the number of times the laser 12 has fired.

In a further feature of the invention, the microprocessor-based pulse height analyzer 59 is used to drive a conventional line printer 57 producing a graph 63 which indicates the size of the particles within the sampling volume 18 at the time the source or laser 12 is fired. Each of the peaks 65, 67 and 69 represent the intensity of the backscattered radiation which is systematically related to the size of the particles in the sampling volume 18 which is transilluminated by substantially identical electromagnetic radiation. Preferably, the abscissa of the graph is marked in units representing the diameter of the particles located.

In order to assist in preventing background radiation from producing specious data at the time the measurements are made, the microprocessor based pulse-height analyzer 59 serves to subtract the background radiation. This is accomplished in the preferred embodiment by subtracting the average of the background pulses, occurring when the source 12 is fired and there are no particles in the sampling volume. More specifically, the size of the particle indicated by peak 65 on the graph would be reduced by the average size of the pulses 71 and 73, which represent the background radiation occurring before and after the measurement of a particle in the sampling volume 68.

Figure 3:
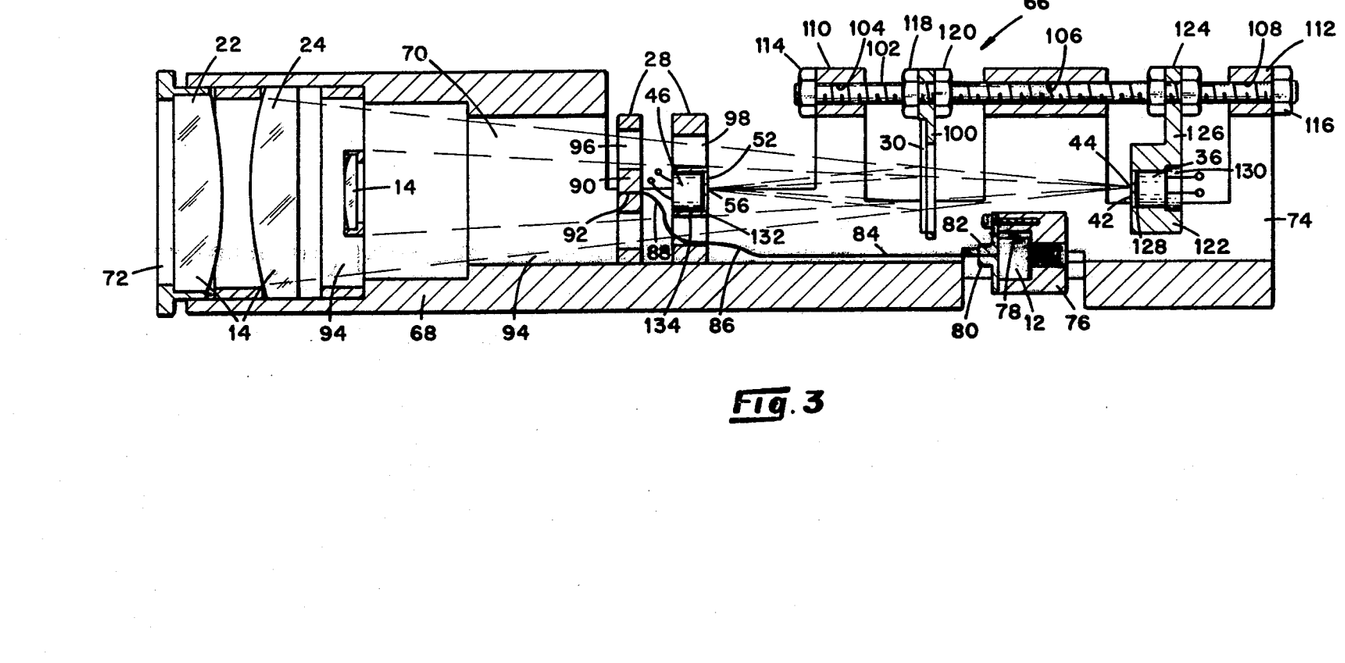
FIG. 3 is a cross sectional view of one embodiment of a sensing head carrying various of the elements of the system and adapted for being positioned proximate a fluid medium having particles of interest suspended therein.

In one embodiment various of the components of the invention are mounted in a suitable sensing head indicated generally at 66 in FIG. 3. The illustrated sensing head 66 is positionable proximate the fluid medium containing the particles to be investigated and includes an elongated frame 68 fabricated from a suitable rigid material. The illustrated frame 68 is substantially cylindrical and defines a cavity 70 along its length which opens at its opposite ends 72 and 74, respectively, of the frame. It will be noted that all of the necessary conducting wires are not shown in FIG. 3 for the sake of ease of understanding the drawings. Also, it should be noted that the various means for mounting the various elements of the sensing head are of small area relative to the total area so as not to present substantial overall obstructions to the passage of light.

In the embodiment of the sensing head illustrated in FIG. 3, the light source 12 is mounted in a suitable cylindrical housing 76 which defines a recess 78 for carrying the portion of the light source 12 such as a diode from which the light is emitted. This housing 68 is provided with a suitable cover 80 and defines an opening 82 therethrough which is adapted for receiving one end portion 84 of the fiber optics cable 86. Light emitted by the source 12 is fed through the optical fiber cable 86 which is positioned at its opposite end 88 substantially along the longitudinal axis of the sensing head 66.

In order to position end 88 of the optical fiber cable 86 along the axis of the sensing head 66 for directing light emitted from the end 88 of the cable, this end 88 of the cable fiber is secured in the substantially cylindrical support 90 defining an opening 92 at its central portion for receiving the end 88 of the cable and positioning this end of the cable along the axis of the sensing head. This support 90 is secured to the inner surface 94 of the wall 68 of the sensing head by an arm (not shown) proportioned to assist in preventing blocking backscattering radiation from passing through cavity 70 toward end 74 of the sensing head 66.

Lenses 14 are positioned in the nose section 94 of the sensing head 66 and adapted to assist in collimating light exiting the end 88 of the optical fiber cable and directing the beam into the fluid medium containing the particles under surveillance.

Light backscattered from particles contained in the fluid medium pass through the annular margins of the lens pair 22 and 24 which serve to direct the backscattered radiation toward the beamsplitter 30. More particularly, a portion of the backscattered radiation passing through the lenses 22 and 24 is directed through the aperture means 28 defining spaced annular apertures 96 and 98 which circumscribe the axis of the sensing head 66 in the illustrated embodiment. Light passing through these apertures 96 and 98 is incident upon a beamsplitter 30 positioned substantially perpendicular to the axis of the sensing head 66. The illustrated beamsplitter 30 is carried by a suitable support 100 adjustably positioned along a shaft 102 mounted on the sensing head frame 68. In this connection, the shaft 102 extends through registering openings 104, 106 and 108 defined in the wall 68 of the sensing head frame 66 and is secured at its opposite ends against supports 110 and 112 by nuts 114 and 116, respectively, received on the opposite ends of the shaft 102. Further, nuts 118 and 120 serve to position the beamsplitter support 100 at a desired location and assist in moving the beamsplitter to preselected positions with respect to the axis of the sensing head.

Light passing through the beamsplitter 30 is incident upon a photodetector means 36 which is carried on a detector support 122 secured at its end 124 to the shaft 102. More specifically, the photodetector means 36 is carried within the cylindrical wall 126 of the detector support 122 and is connected through conductors (not shown) to suitable indicator means 58 shown diagrammatically in FIG. 1.

The diameter and length of the portion of the fluid medium from which backscattered radiation is accepted by the photodetector means 36 is determined by suitable aperture means 42 positioned substantially perpendicular to the axis of the sensing head 66 and secured at end 128 of the cylindrical opening 130 in which the photodetector means 36 is positioned.

The backscattered electromagnetic radiation reflected by the beamsplitter 30 is directed toward further photodetector means 46 positioned substantially along the axis of the sensing head 66 and mounted in a suitable opening 132 provided in support 134. This photodetector means 46 is connected through suitable electrical connectors (not shown) to the indicator means 58 which serves to compare the signals generated by the first and further photodetector means 36 and 46, respectively, for indicating the size of a particle contained in the region 18. More specifically, to assist in assuring particles under the first region or sampling volume 18 at the time the measurements are made, the intensity of the light backscattered from the further region or sampling volume 54 disposed in the fluid medium and containing the first region 18 is compared with the intensity of the light backscattered from the first region. Measurements are made if and only if the intensity from the further region 54 is substantially identical to the intensity from the first region 18, (where the transfer functions of the measuring apparatus associated with each channel is identical) thereby assuring the absence of particles within the region 62 outside the first region. It will be recognized that where the transfer function of the measuring apparatus or the amount of light passed and reflected by the beamsplitter 30 is not identical then corresponding adjustments may be made in the programming of the microprocessor based analyzer to avoid the accumulation of specious data.

The size and shape of the sampling volume 54 is defined by aperture means 52 which is positioned substantially perpendicular to the axis of the sensing head 66 at a spaced location from the surface 47 of the photosensitive means 46. The dimensions of the aperture 56 define the length and width of the area in fluid medium from which light backscattered from particles positioned in such sampling volume is received by the photosensitive means 46 as pointed out in more detail hereinabove.

From the foregoing detailed description it will be recognized that an improved in situ electro-optical particle measuring system and method are provided which have certain advantages over prior art devices. For example, the disclosed system includes an intermittently interrupted source of electromagnetic radiation for providing the incident illumination of particles suspended in a fluid medium. This source which may include a pulsating gas laser is relatively inexpensive to operate and service. Moreover, to assist in assuring substantially uniform illumination of the particles prior to taking measurements, the intensities of the radiation backscattered from two regions, one which is contained within the other, are compared to assure residence of the particles under surveillance within the smaller of the regions at the time the measurements are made, this smaller region having substantially uniform incident illumination.

While a preferred embodiment has been shown and described, it will be understood that there is no intention to limit the invention by such disclosure, but rather it is intended to cover all modifications and alternate constructions falling within the spirit and scope of the invention as defined in the appended claims and equivalents thereof.

What is claimed is:

1. An electro-optical system for in situ measurement of the size of particles suspended in a fluid medium moving relative to said system, said system comprising a source of intermittently interrupted beam of electromagnetic radiation, means for directing said interrupted beam of radiation from said source through a portion of said fluid medium, first photodetector means having a first photosensitive medium for producing first electronic signals systematically related to the intensity of electromagnetic radiation falling on said first photosensitive medium, first optical means optically defining a first region having an outer perimeter in said fluid medium illustrated by said interrupted beam of radiation whereby a portion of the radiation scattered by a particle situated in said first region is incident on said first photosensitive medium, said first region being positioned substantially centrally of said beam whereby the illumination across said first region is substantially uniform, further photodetector means having a further photosensitive medium for producing further electronic detection signals systematically related to the intensity of electromagnetic radiation falling on said further photosensitive medium, further optical means optically defining in said fluid medium illuminated by said interrupted beam of radiation a further region having an outer perimeter that is larger than and spaced apart from the outer perimeter of said first region and which fully encompasses said first region, said outer perimeters defining therebetween a space which is fully within the outer perimeter of said second region and fully outside the outer perimeter of said first region and containing said first region whereby a portion of the radiation scattered by a particle situated in said further region is incident on said further photosensitive medium, indicator means responsive to said first and further electronic detection signals for determining when a particle under surveillance is residing within said first region, for indicating the size of said particle per unit volume of fluid medium.

2. A system according to claim 1 wherein said source is a pulsating laser.

3. A system according to claim 1 wherein said first and further optical means collects radiation backscattered by a particle.

4. A system according to claim 3 wherein said first and further optical means collects electromagnetic radiation backscattered at about 170°.

5. A system according to claim 3 wherein said first and further optical means collect electromagnetic radiation backscattered within a range of about 5°.

6. A system according to claim 3 wherein said first and further optical means includes an aperture for collecting backscattered radiation symmetrically around said beam.

7. A system according to claim 3 wherein said first and further optical means include an annular aperture concentric with said beam for collecting a portion of the electromagnetic radiation backscattered, beam splitter means disposed coaxially of said beam on the opposite side of said source for passing a predetermined portion of the radiation incident on said beam splitter, the angle of incidence of backscattered radiation incident on said beam splitter being substantially equal to the angle of emergence of the portion of radiation traversing said beam splitter, and for reflecting a predetermined portion of the radiation incident on beam splitter, optical lens means for receiving backscattered radiation and for directing said radiation onto said beam splitter means and thence onto said first and further photosensitive medium, first aperture means disposed intermediate said beam splitter and first photodetector means for passing a predetermined portion of the radiation traversing said beam splitter onto said first photosensitive medium, further aperture means disposed intermediate said beam splitter and said further photodetector means for passing a predetermined portion of the radiation reflected from said beam splitter onto said further photosensitive medium whereby the image plane of said first optically defined region is coincident with said first aperture means and the image plane of said further optically defined region is coincident with said further aperture means.

8. A system according to claim 3 wherein said indicator means compares the first and further electronic detection signals for indicating the size of the particles positioned in said first optically defined region.

9. The system according to claim 3 wherein said means for directing said beam of radiation from said source through a portion of said fluid medium comprises an optical fiber cable fed at one of its ends by said source, the opposite end of said cable being positioned for directing said beam of radiation along a predetermined path through a portion of said fluid medium and collimating optical means interposed in the path of said beam between said source and said fluid medium to assist in forming said beam.

10. A method for measuring in situ the size of particles suspended in a fluid medium, said method comprising the steps of directing a beam of electromagnetic radiation through a portion of said medium, detecting the intensity of the radiation scattered from a first optically defined region having an outer perimeter transilluminated by incident radiation having substantially uniform incident intensity, producing first detection signals systematically related to the intensity of the radiation scattered from said first optically defined region, detecting the intensity of the radiation scattered from a further optically defined region having an outer perimeter that is larger than and spaced apart from the outer perimeter of said first region and which fully encompasses said first region, said outer perimeters defining therebetween a space which is fully within the outer perimeter of said second region and fully outside the outer perimeter of said first region and containing said first optically defined region, producing further detection signals systematically related to said intensity of the radiation scattered from said further optically defined region, and utilizing said first and further detection signals to provide an indication of the size and distribution of said particles per unit volume of said medium.

11. A method according to claim 10 wherein said beam is periodically interrupted.

12. A method according to claim 10 wherein the background radiation of said detection signals is substantially eliminated to enhance the accuracy of the measurements.

13. A method according to claim 10 wherein said beam is interrupted at predetermined periods having durations which are slightly greater than the duration required for individual particles suspended in the fluid medium to transverse said first optically defined region.

* * * * *

UNITED STATES PATENT OFFICE
CERTIFICATE OF CORRECTION

Patent No. 4,140,395  Dated February 20, 1979

Inventor(s) Gerhard Kreikebaum

It is certified that error appears in the above-identified patent and that said Letters Patent are hereby corrected as shown below:

Claim 1. Column 12, Line 4, change "illustrated" to -- illuminated --.

Signed and Sealed this

Twenty-second Day of May 1979

[SEAL]

Attest:

RUTH C. MASON  
*Attesting Officer*

DONALD W. BANNER  
*Commissioner of Patents and Trademarks*